US007005443B1

(12) United States Patent
May et al.

(10) Patent No.: US 7,005,443 B1
(45) Date of Patent: Feb. 28, 2006

(54) 5-HYDROXY INDAZOLE DERIVATIVES FOR TREATING GLAUCOMA

(75) Inventors: Jesse A. May, Fort Worth, TX (US); Zixia Feng, Arlington, TX (US)

(73) Assignee: Alcon, Inc., Hunenberg (CH)

( * ) Notice: Subject to any disclaimer, the term of this patent is extended or adjusted under 35 U.S.C. 154(b) by 114 days.

(21) Appl. No.: 10/220,988

(22) PCT Filed: Nov. 14, 2000

(86) PCT No.: PCT/US00/31143

§ 371 (c)(1),
(2), (4) Date: Sep. 6, 2002

(87) PCT Pub. No.: WO01/70701

PCT Pub. Date: Sep. 27, 2001

Related U.S. Application Data

(60) Provisional application No. 60/190,283, filed on Mar. 17, 2000.

(51) Int. Cl.
*A61K 31/415* (2006.01)

(52) U.S. Cl. .................................................. 514/403
(58) Field of Classification Search ................. 514/403
See application file for complete search history.

(56) References Cited

U.S. PATENT DOCUMENTS

| | | | |
|---|---|---|---|
| 4,690,931 A | 9/1987 | Wick et al. | |
| 5,151,444 A | 9/1992 | Ueno et al. | |
| 5,276,051 A | 1/1994 | Lesieur et al. | |
| 5,296,504 A | 3/1994 | Stjernschantz et al. | |
| 5,352,708 A | 10/1994 | Woodward et al. | |
| 5,422,368 A | 6/1995 | Stjernschantz et al. | |
| 5,494,928 A * | 2/1996 | Bos ........................... | 514/415 |
| 5,571,833 A * | 11/1996 | Kruse et al. ................ | 514/414 |
| 5,874,477 A | 2/1999 | McConnell et al. | |
| 5,889,052 A | 3/1999 | Klimko et al. | |
| 5,902,815 A | 5/1999 | Olney et al. | |
| 6,391,872 B1 * | 5/2002 | Marfat ....................... | 514/218 |
| 6,664,286 B1 * | 12/2003 | May et al. .................. | 514/415 |
| 6,696,476 B1 * | 2/2004 | Chen et al. ................. | 514/403 |

FOREIGN PATENT DOCUMENTS

| | | |
|---|---|---|
| WO | WO 94/13275 A1 | 6/1994 |
| WO | WO 98/30548 | 7/1998 |
| WO | WO 98/31354 A2 | 7/1998 |
| WO | WO 98/31354 A3 | 7/1998 |
| WO | WO 99/59499 A2 | 11/1999 |
| WO | WO 99/59499 A3 | 11/1999 |
| WO | 00/12482 * | 3/2000 |
| WO | 00/16761 * | 3/2000 |
| WO | WO 00/12482 A2 | 3/2000 |
| WO | WO 00/12482 A3 | 3/2000 |
| WO | WO 00/16761 A2 | 3/2000 |
| WO | WO 00/16761 A3 | 3/2000 |

OTHER PUBLICATIONS

Ainsworth, C., "Substituted β-Aminoethylindazoles", J. Amer. Chem. Soc., 80:965-967 (1958).
Ainsworth, C., "The Indazole Analog Of Serotonin", Journal Of The American Chemical Society, vol. 79, pp 5245-5247 (1957) [XP-000881644] [D2].
Bennetau, B., et al., "Une Voie De Synthese Simple Et Rapide De Phenols Meta Acyles", Tetrahedron, 50:1179-1188 (1994).
Bodar, Nicholas, et al., "Improved Delivery Through Biological Membranes, XVII3. A Site-Specific Chemical Delivery System as a Short-Acting Mydriatic Agent", Pharm. Res., 168-173 (1984).
Bowen et al., "Nonlinear regression using spreadsheets", Trends In Pharmacological Sciences, 16:413 (1995).
Buchheit, K-H, et al., "The Serotonin 5-HT4 Receptor. 2. Structure—Activity Studies of the Indole Carbazimidiamide Class of Agonists1", J. Med. Chem., 38:2331-2338 (1995).
Chemical Abstract, 1988:94460, "Synthesis and radioprotective activity of .beta.-(3-indazolyl)ethylamine derivatives" [XP002162456,] [D3].
Fiorella, et al., "Role of 5-HT2A and 5-HT2C receptors in the stimulus effects of hallucinogenic drugs II: reassessment of LSD false positives", Psychopharmacology, 121:357 (1995).
Griffin, B. W., et al., "Pharmacological Characterization of an FP Prostaglandin Receptor on Rat Vascular Smooth Muscle Cells (17r5) Coupled to Phosphoinositide Turnover and Intracellular Calcium Mobilization", J. Pharmacol. Exp. Ther., 286:411-418 (1998).
Gupta, Y.K., et al., "Therapeutic Potentials of 5-HT Receptor Modulators", Indian Journal Of Pharmacology, vol. 26, No. 2, pp 94-107 (Jun. 1, 1994) [D6].
Hamano, H. and Okuda, S., "Studies on Dimethoxyphenylaminoalcohols. II. 1) Syntheses and Relative Configurations of 1-Dimethoxyphenyl-3-(alkylamino) butanols", Chem. Parm. Bull., 22:1348-1359 (1974).
Johnson, M. P., et al., "Binding To The Serotonin 5-HT2 Receptor By The Enantioners of 125I-DOI", Neuropharmacology, 26:1803-1806 (1987).
Sakito, et al., "Asymmetric Reduction Of Oxime Ethers. Distinction Of Anti And Syn Isomers Leading To Enantiomeric Amines", Tetrahedron Letters, 29:223-224 (1988).
Villalobos, A., et al., "Novel Benzisoxazole Derivatives as Potent and Slective Inhibitors of Acetylcholinesterase", J. Med. Chem., 37:2721-2734 (1994).
Wilkerson et al., "Anti-inflammatory phospholipase-A2 inhibitors. II. Design, synthesis and structure-activity relationship", Eur. J. Med. Chem., 27:595-610 (1992).

(Continued)

*Primary Examiner*—Kevin E. Weddington
(74) *Attorney, Agent, or Firm*—Patrick M. Ryan

(57) ABSTRACT

3-(2-aminoethyl)-1H-indazol-5-ols useful for treating elevated intraocular pressure and glaucoma are disclosed.

5 Claims, No Drawings

OTHER PUBLICATIONS

Wrona, M. Z. and Dryhurst, Glenn, "Further Insights into the Oxidation Chemistry of 5-Hydroxytryptamine", Journal of Pharmaceutical Sciences, 77:911-917 (1988).

Wrona, M. Z. and Dryhurst, G., "Oxidation Chemistry of 5-Hydroxytryptamine. 1. Mechanism and Products Formed at Micromoloar Concentrations" J. Org. Chem, 52:2817-2825 (1987).

Banerji, A., et al., "Synthesis Of 2-Hydroxy-4, 6-Dimethoxycrotonophenone A New Class Of Natural Products From Dysophylla Stellata Benth.", Synthetic Communications, 10(11):851-856 (1980).

Bruce, D., B., et al., "Reactions in Fused Aluminium Chloride-Sodium Chloride", Journal of The Chemical Society, 2403-2406 (1953).

Buchanan, G. L., "The Dakin-West Reaction", Chem. Soc. Rev., 17:91-109 (1988).

"Improved Ocular Drug Delivery with Prodrugs", Drugs And The Pharmaceutical Sciences, edited by Kenneth B. Sloan, vol. 53:221-254 (1992).

Peshkovsky, A. and McDermott, A. E., NMR Spectroscopy in the Presence of Strong Ac Electric Fields: Degree of Alignment of Polar Molecules, J. Phys. Chem., 103:8604-8611 (1999).

Wrona, M.Z. and Dryhurst, G., "Oxidation of Serotonin by Superoxide Radical: Implications to Neurodegenerative Brain Disorders", Chem. Res. Toxicol., 11(6):639-650 (1998).

* cited by examiner

5-HYDROXY INDAZOLE DERIVATIVES FOR TREATING GLAUCOMA

This application is a National Stage Application of PCT/US00/31143, filed Nov. 14, 2000, which claims priority from U.S. Provisional Patent Application No. 60/190,283, filed Mar. 17, 2000.

The present invention is directed to substituted 3-(2-aminoethyl)-1H-indazol-5-ols, some of which are novel, for lowering and controlling normal or elevated intraocular pressure (IOP) and treating glaucoma.

BACKGROUND OF THE INVENTION

The disease state referred to as glaucoma is characterized by a permanent loss of visual function due to irreversible damage to the optic nerve. The several morphologically or functionally distinct types of glaucoma are typically characterized by elevated IOP, which is considered to be causally related to the pathological course of the disease. Ocular hypertension is a condition wherein intraocular pressure is elevated but no apparent loss of visual function has occurred; such patients are considered to be a high risk for the eventual development of the visual loss associated with glaucoma. Some patients with glaucomatous field loss have relatively low intraocular pressure. These so called normotension or low tension glaucoma patients can also benefit from agents that lower and control IOP. If glaucoma or ocular hypertension is detected early and treated promptly with medications that effectively reduce elevated intraocular pressure, loss of visual function or its progressive deterioration can generally be ameliorated. Drug therapies that have proven to be effective for the reduction of intraocular pressure include both agents that decrease aqueous humor production and agents that increase the outflow facility. Such therapies are in general administered by one of two possible routes, topically (direct application to the eye) or orally.

There are some individuals who do not respond well when treated with certain existing glaucoma therapies. There is, therefore, a need for other topical therapeutic agents that control IOP.

It has been found that serotonergic compounds which possess agonist activity at $5\text{-}HT_2$ receptors effectively lower and control normal and elevated IOP and are useful for treating glaucoma, see commonly owned co-pending application, PCT/US99/19888. Compounds that act as agonists at $5\text{-}HT_2$ receptors are well known and have shown a variety of utilities, primarily for disorders or conditions associated with the central nervous system (CNS). U.S. Pat. No. 5,494,928 discloses certain 2-(indol-1-yl)-ethylamine derivatives that are $5\text{-}HT_{2c}$ agonists for the treatment of obsessive compulsive disorder and other CNS derived personality disorders. U.S. Pat. No. 5,571,833 discloses tryptamine derivatives that are $5\text{-}HT_2$ agonists for the treatment of portal hypertension and migraine. U.S. Pat. No. 5,874,477 discloses a method for treating malaria using $5\text{-}HT_{2A/2C}$ agonists. U.S. Pat. No. 5,902,815 discloses the use of $5\text{-}HT_{2A}$ agonists to prevent adverse effects of NMDA receptor hypo-function. WO98/31354A2 discloses $5\text{-}HT_{2B}$ agonists for the treatment of depression and other CNS conditions. Agonist response at the $5\text{-}HT_{2A}$ receptor is reported to be the primary activity responsible for hallucinogenic activity, with some lesser involvement of the $5\text{-}HT_{2c}$ receptor possible [Psychopharmacology, Vol. 121:357, 1995].

The present invention is directed to substituted 3-(2-aminoethyl)-1H-indazol-5-ols, some of which are novel. It is believed that these compounds will have a high affinity for and function as agonists at the serotonergic $5\text{-}HT_2$ receptor, and will thereby be useful for lowering and controlling normal or elevated intraocular pressure (IOP) and treating glaucoma. When a phenolic moiety is included in this substitution, e.g. a hydroxyl group at indazole ring position five, such compounds can be particularly sensitive to oxidation reactions well known to occur with phenolic compounds in general, including the related hydroxytryptamines [J. Phys. Chem. 103, 8606 (1999), Chem. Res. Toxicol. 11, 639 (1998), J. Org. Chem. 52, 2817 (1987), J. Pharm. Sci. 77, 911 (1988)], which are of particular relevance to the present application. Protection of such hydroxy substituted phenols from oxidation can be accomplished by derivatization of the aryl hydroxy group to provide a suitable ester, carbamate, or carbonate. Though the ester, carbamate, or carbonate derivatives do not themselves possess a high affinity for the above mentioned receptors, they do have utility in the treatment of glaucoma since suitably protected phenols can be cleaved in vivo either by chemical hydrolysis or through the action of tissue esterases. Such cleavage would deliver the desired therapeutic agent, that is, the desired novel 5-hydroxy-indazole compounds of the present invention. The concept of utilizing such derivatized phenolic compounds as chemical delivery agents is well known in the art [Drugs Pharm. Sci. 53, 221 (1992), Pharm. Res., 168 (1984)].

The chemical synthesis of 3-(2-dimethylamino-ethyl)-1H-indazol-5-ol has been reported with no comment on the utility of the compound [J. Amer. Chem. Soc. 79, 5245–5247 (1957); J. Amer. Chem. Soc. 80, 965 (1958)].

The chemical synthesis of 1-(2-aminopropyl)-1H-indazol-6-ol and other ring substitution variants has been reported in published International Patent Application No. WO98/30548 (1998). The utility cited for the compounds of this application is for treating central nervous system diseases such as sexual disorders, genital insufficiency, appetite regulation disorders, anxiety, depression, and sleep disorders. There is no contemplation of ophthalmic use noted in this application. Published International Patent Application No. WO00/12482 (2000) discloses certain 1-(indazol-3-yl)-2-propylamine derivatives that are $5\text{-}HT_2$ agonists for the treatment of disorders of the central nervous system.

SUMMARY OF THE INVENTION

The present invention is directed to derivatives of 3-(2-aminoethyl)-1H-indazol-5-ol, some of which are novel, which can be used to lower and control IOP associated with normal-tension glaucoma, ocular hypertension, and glaucoma in warm blooded animals, including man. The compounds are formulated in pharmaceutical compositions suitable for topical delivery to the eye.

DESCRIPTION OF THE PREFERRED EMBODIMENTS

Compounds that are useful according to the present invention are represented by the following Formula I.

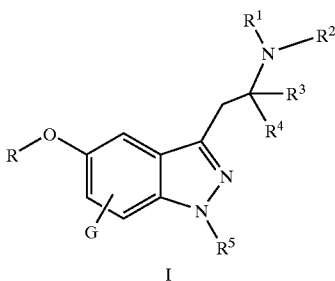

FORMULA I wherein G is chosen from hydrogen, halogen, or $C_{1-4}$alkyl;
R is hydrogen, $C_{1-4}$alkyl, C(=O)W, or P(=O)(OX)(OY), $R^1$ and $R^2$ are hydrogen;
$R^3$ and $R^4$ are independently chosen from hydrogen, $C_{1-4}$alkyl or $R^3$, $R^4$ and the carbon atom to which they are attached can form a cyclopropyl ring, or furthermore, $R^2$ and
$R^3$ together can be $(CH_2)_m$ to form a saturated heterocycle;
when $R^2$ and $R^3$ are part of a heterocycle, $R^1$ can be hydrogen or $C_{1-4}$alkyl;
$R^5$ can be hydrogen or $C_{1-4}$alkyl;
when R, $R^1$, $R^2$, $R^5$, and G all are hydrogen $R^3$ and $R^4$ cannot both be hydrogen;
W is $C_{1-6}$alkyl, $NR^6R^7$, $N(R^6)CH_2(CH_2)_nC(=O)N(R^7)(R^8)$, $OC_{1-6}$ alkyl, $C_{1-6}$alkyl (which can be substituted with halogen, hydroxyl, $CO_2C_{1-4}$alkyl, $CON(C_{1-4}$alkyl$)_2$, C(=NH)NH$_2$, HC(=NH)NH$_2$, NH$_2$), $C_{2-4}$alkenyl (substituted by phenyl, unsubstituted or substituted with one or more of $C_{1-4}$alkyl, $C_{1-4}$alkoxy or halogen);
$R^6$, $R^7$, $R^8$ are independently chosen from hydrogen or $C_{1-4}$alkyl;
X and Y are independently chosen from hydrogen, $C_{1-10}$ alkyl or X and Y can together form a lower alkyl chain of $(CH_2)_m$;
m is 2–4;
n is 1 or 2;

and pharmaceutically acceptable salts and solvates of the compounds of Formula I.

Compounds that are novel and which are useful according to the present invention can be defined as follows:
G is chosen from hydrogen, halogen, or $C_{1-4}$alkyl;
R is C(=O)W, or P(=O)(OX)(OY), $R^1$ and $R^2$ are hydrogen;
$R^3$, $R^4$ and the carbon atom to which they are attached can form a cyclopropyl ring, or furthermore, $R^2$ and $R^3$ together can be $(CH_2)_m$ to form a saturated heterocycle;
when $R^2$ and $R^3$ are part of a heterocycle, $R^1$ can be hydrogen or $C_{1-4}$-alkyl;
$R^5$ can be hydrogen or $C_{1-4}$alkyl;
W is $C_{1-6}$alkyl, $NR^6R^7$, $N(R^6)CH_2(CH_2)_nC(=O)N(R^7)(R^8)$, $OC_{1-6}$alkyl, $C_{1-6}$alkyl (which can be substituted with halogen, hydroxyl, $CO_2C_{1-4}$alkyl, $CON(C_{1-4}$alkyl$)_2$, C(=NH)NH$_2$, HC(=NH)NH$_2$, NH$_2$), $C_{2-4}$alkenyl (substituted by phenyl, unsubstituted or substituted with one or more of $C_{1-4}$alkyl, $C_{1-4}$alkoxy or halogen);
$R^6$, $R^7$, $R^8$ are independently chosen from hydrogen or $C_{1-4}$alkyl;
X and Y are independently chosen from hydrogen, $C_{1-10}$ alkyl or X and Y can together form a lower alkyl chain of $(CH_2)_m$;
m is 2–4;
n is 1 or 2.

Preferred Compounds are:
G is chosen from hydrogen, halogen, or $C_{1-4}$alkyl;
R is hydrogen, C(=O)W, or P(=O)(OX)(OY), $R^1$ and $R^2$ are hydrogen;
$R^3$ and $R^4$ are independently chosen from hydrogen, $C_{1-4}$alkyl or $R^3$, $R^4$ and the carbon atom to which they are attached can form a cyclopropyl ring;
$R^5$ can be hydrogen or $C_{1-4}$alkyl;
W is $C_{1-6}$alkyl, $NR^6R^7$, $N(R^6)CH_2(CH_2)_nC(=O)N(R^7)(R^8)$, $C_{1-6}$alkyl (which can be substituted with halogen, hydroxyl, $CO_2C_{1-4}$alkyl, $CON(C_{1-4}$alkyl$)_2$, C(=NH)NH$_2$HC(=NH)NH$_2$, NH$_2$), $C_{2-4}$alkenyl (substituted by phenyl, unsubstituted or substituted with one or more of $C_{1-4}$alkyl, $C_{1-4}$alkoxy or halogen);
$R^6$, $R^7$, $R^8$ are independently chosen from hydrogen or $C_4$alkyl;
X and Y are independently chosen from hydrogen, $C_{1-10}$ alkyl or X and Y can together form a lower alkyl chain of $(CH_2)_m$;
m is 2 or 3;
n is 1 or 2.

Most Preferred Compounds are:
G is chosen from hydrogen, halogen, or $C_{1-4}$alkyl;
R is hydrogen or C(=O)W;
$R^1$ and $R^2$ are hydrogen;
$R^3$ is hydrogen and $R^4$ is methyl or $R^3$, $R^4$ and the carbon atom to which they are attached form a cyclopropyl ring;
$R^5$ is hydrogen;
W is $C_{1-6}$alkyl, $C_{1-6}$alkyl (which can be substituted with halogen, hydroxyl, $CON(C_{1-4}$alkyl$)_2$, C(=NH)NH$_2$).

Representative Examples of Preferred Novel Compounds of Formula I are:
3-(2-Aminopropyl)-1H-indazol-5-ol;
3-(2-Aminopropyl)-1-methyl-1H-indazol-5-ol;
2-(5-Methoxy-1H-indazol-3-yl)-1-methyl-ethylamine;
3-(2-Aminopropyl)-6-fluoro-1H-indazol-5-ol;
3-(2-Aminopropyl)-7-methyl-1H-indazol-5-ol;
3-(2-Aminopropyl)-6-fluoro-1-methyl-1H-indazol-5-ol;
2-Methyl-propionic acid 3-(2-aminopropyl)-1H-indazol-5-yl ester;
2,2-Dimethyl-propionic acid 3-(2-aminopropyl)-1H-indazol-5-yl ester;
Cyclopropanecarboxylic acid 3-(2-aminopropyl)-1H-indazol-5-yl ester;
N,N-Diethyl-succinamic acid 3-(2-aminopropyl)-1H-indazol-5-yl ester It is recognized that compounds of Formula I can contain one or more chiral centers. This invention contemplates all enantiomers, diastereomers and, mixtures thereof.

In the above definitions, the total number of carbon atoms in a substituent group is indicated by the $C_{i-j}$ prefix where the numbers i and j define the number of carbon atoms; this definition includes straight chain, branched chain, and cyclic alkyl or (cyclic alkyl)alkyl groups.

It is important to recognize that a substituent may be present either singly or multiply when incorporated into the indicated structural unit. For example, the substituent halogen, which means fluorine, chlorine, bromine, or iodine, would indicate that the unit to which it is attached may be substituted with one or more halogen atoms, which may be the same or different.

Synthesis

The compounds of Formula I can be prepared by using one of several synthetic procedures. For example, condensation of the suitably substituted indazol-3-carboxaldehyde (1), which can be prepared from the corresponding indazole by known methods [J. Med. Chem. 38, 2331 (1995)], with the appropriate nitroalkane gives the corresponding nitroalkene (2), which can be reduced with, e.g. LiAlH$_4$, and if desired dealkylated with, e.g. boron tribromide, to provide the desired compounds 3 of Formula I.

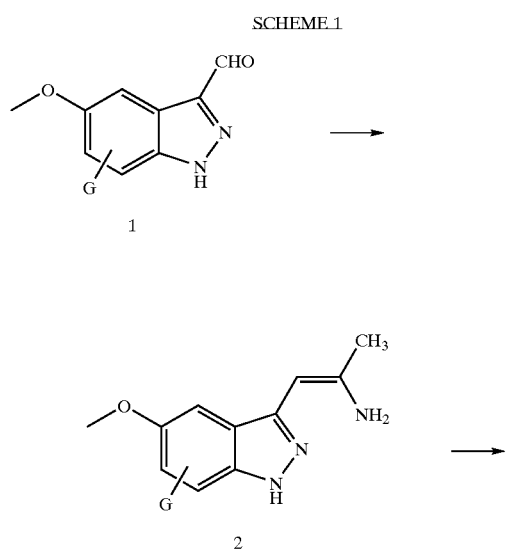

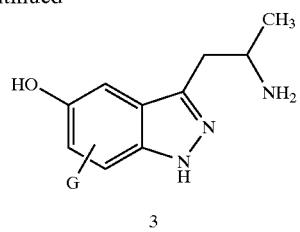

Another procedure for preparing compounds of Formula I is outlined in Scheme 2. The appropriately substituted 2-fluoro-acetophenone (4), either purchased or prepared by known procedures, e.g. Tetrahedron 50, 1179 (1994), can be reacted with the desired aldehyde, such as acetaldehyde, in the presence of a strong base, e.g. lithium diisopropylamide, to give the aryl β-hydroxyalkyl ketone (5) [Synth. Commun. 10, 851 (1980)], which can be reacted with anhydrous hydrazine by known methods to provide the substituted indazole 6 [J. Med. Chem. 37, 2721 (1994)]. Conversion of the secondary alcohol moiety of 6 to the desired primary amine can be accomplished using the well known sequence involving initial activation by formation of a sulfonate ester followed by displacement of this ester by reaction with sodium azide, and finally reduction of the azide with concomitant removal of any phenol protective groups, e.g. benzyl, to provide the desired amine (3). Alternately, compound 4 can be reacted with an aldehyde, e.g. acetaldehyde, under acidic conditions to provide the chalcone intermediate, e.g. 7 [J. Chem. Soc., 2403 (1953)] (Scheme 3). Addition of a suitably protected amine, e.g. benzylamine, to the double bond of 7 provides the desired amino ketone 8 [Chem. Pharm. Bull. 22, 1348 (1974)] which when treated with hydrazine provides the substituted indazole 9 [J. Med. Chem. 37, 2721 (1994)]; removal of the protective groups by hydrogenolysis provides the desired compounds 3.

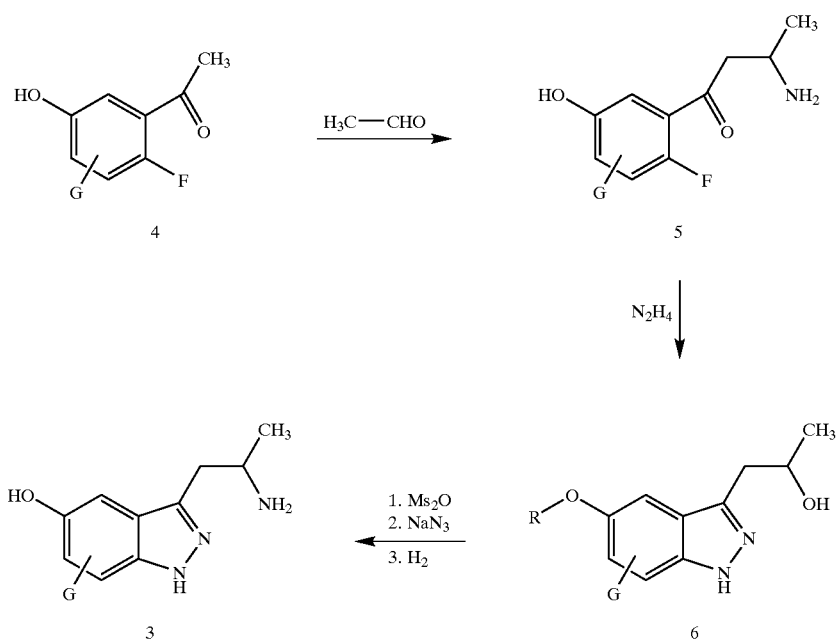

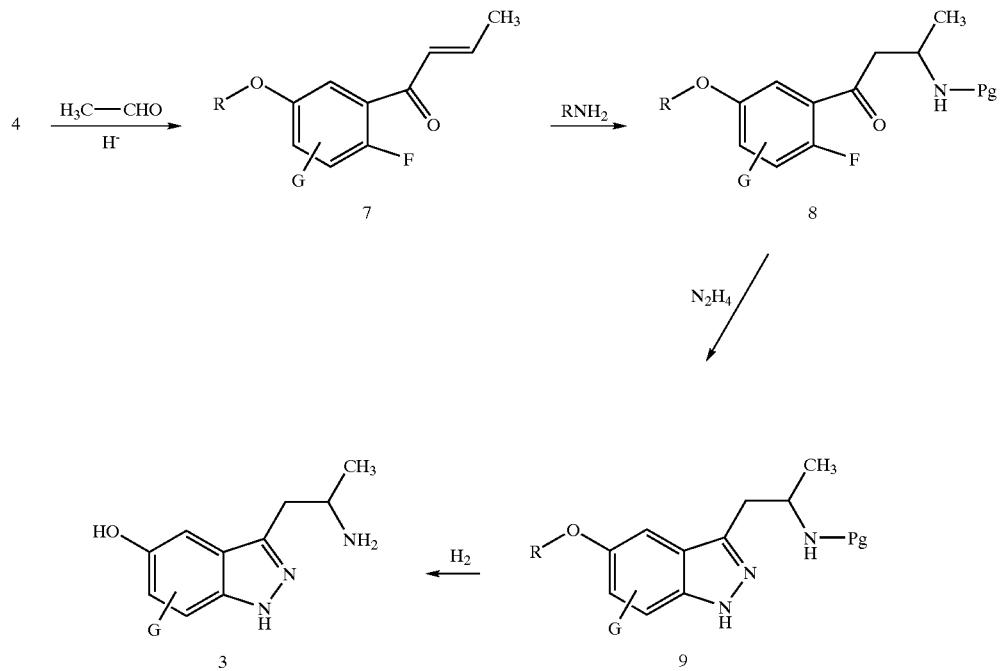

Yet another procedure for preparing compounds of Formula I, but beginning with (5-benzyloxy-1H-indazol-3-yl)-acetic acid (10) [J. Amer. Chem. Soc. 79, 5246 (1957)] as the starting material, is outlined in Scheme 4. Reaction of 10 with acetic anhydride in the presence of the appropriate base under Dakin-West conditions [Chem. Soc. Rev., 17, 91 (1988)] provides intermediate 11 which upon reaction with O-methyl-hydroxylamine gives the oxime 12. Reduction of the 12, e.g. with borane, will provide the desired compounds 13 of Formula I [Eur. J. Med. Chem. 27, 595 (1992), Tetrahedron, 29, 223 (1988)].

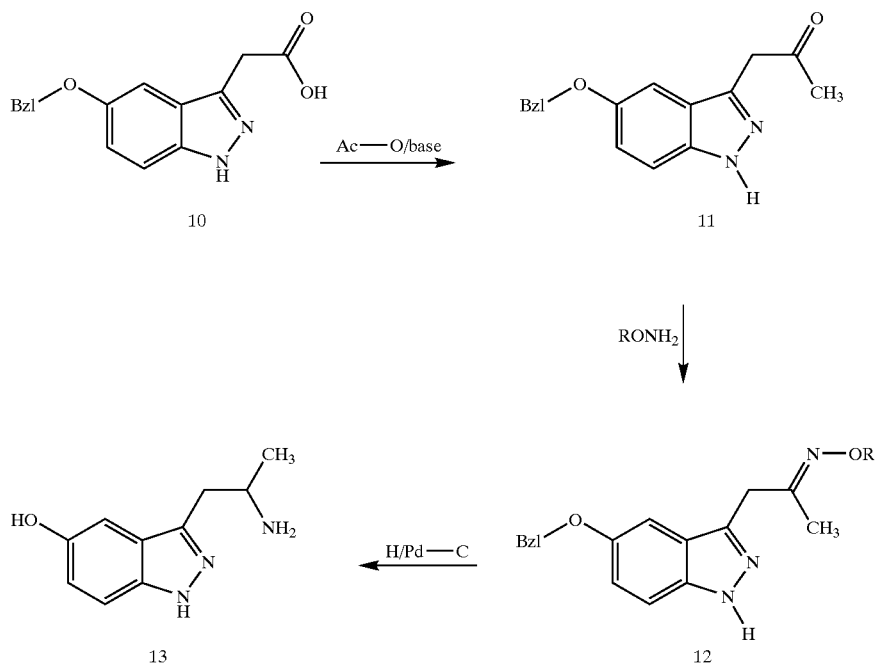

Compounds of Formula I, wherein R is C(=O)W, can be prepared by reacting the appropriate indazole 3, or preferably a suitable amino-protected intermediate, e.g. 14 (Scheme 5) with the desired activated acid derivative, such as an acid halide or active ester, or the like, to provide the esters 15. Removal of the N-protective group from the intermediate 15 provides the desired compounds 16 of Formula 1.

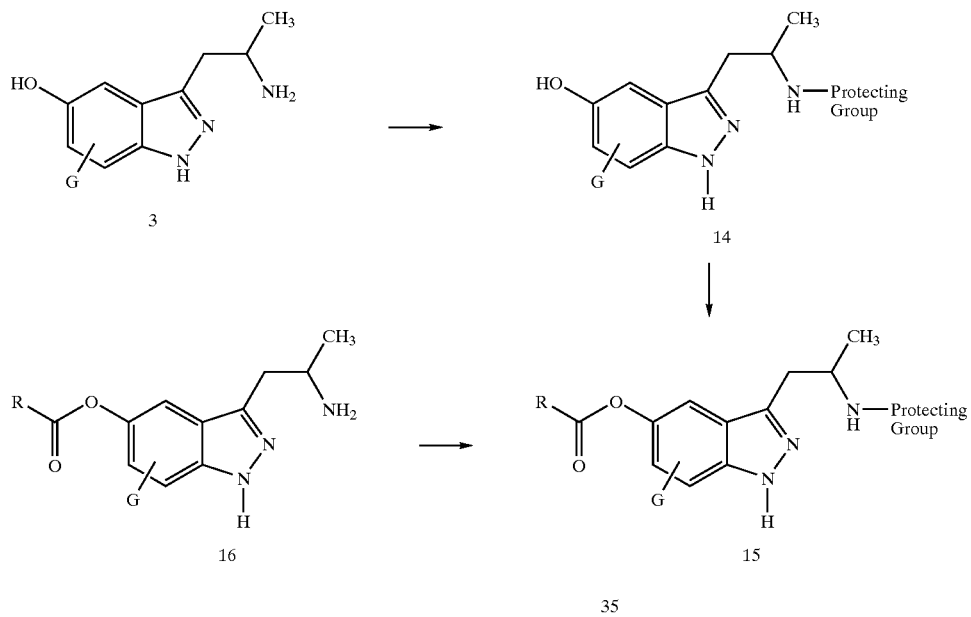

SCHEME 5

The compounds of this invention, Formula I, can be incorporated into various types of ophthalmic formulations for delivery to the eye (e.g., topically, intracamerally, or via an implant). The compounds are preferably incorporated into topical ophthalmic formulations for delivery to the eye. The compounds may be combined with ophthalmologically acceptable preservatives, surfactants, viscosity enhancers, penetration enhancers, buffers, sodium chloride, and water to form an aqueous, sterile ophthalmic suspension or solution. Ophthalmic solution formulations may be prepared by dissolving a compound in a physiologically acceptable isotonic aqueous buffer. Further, the ophthalmic solution may include an ophthalmologically acceptable surfactant to assist in dissolving the compound. Furthermore, the ophthalmic solution may contain an agent to increase viscosity, such as, hydroxymethylcellulose, hydroxyethylcellulose, hydroxypropylmethylcellulose, methylcellulose, polyvinylpyrrolidone, or the like, to improve the retention of the formulation in the conjunctival sac. Gelling agents can also be used, including, but not limited to, gellan and xanthan gum. In order to prepare sterile ophthalmic ointment formulations, the active ingredient is combined with a preservative in an appropriate vehicle, such as, mineral oil, liquid lanolin, or white petrolatum. Sterile ophthalmic gel formulations may be prepared by suspending the active ingredient in a hydrophilic base prepared from the combination of, for example, carbopol-974, or the like, according to the published formulations for analogous ophthalmic preparations; preservatives and tonicity agents can be incorporated.

The compounds are preferably formulated as topical ophthalmic suspensions or solutions, with a pH of about 5 to 8. The compounds will normally be contained in these formulations in an amount 0.01% to 5% by weight, but preferably in an amount of 0.25% to 2% by weight. Thus, for topical presentation 1 to 2 drops of these formulations would be delivered to the surface of the eye 1 to 4 times per day according to the discretion of a skilled clinician.

The compounds can also be used in combination with other agents for treating glaucoma, such as, but not limited to, β-blockers (e.g., timolol, betaxolol, levobetaxolol, carteolol, levobunolol, propranolol), carbonic anhydrase inhibitors (e.g., brinzolamide and dorzolamide), $\alpha_1$ antagonists (e.g. nipradolol), $\alpha_2$ agonists (e.g., iopidine and brimonidine), miotics (e.g., pilocarpine and epinephrine), prostaglandin analogs (e.g., latanoprost, travaprost, unoprostone, and compounds set forth in U.S. Pat. Nos. 5,889,052; 5,296,504; 5,422,368; and 5,151,444, "hypotensive lipids" (e.g., lumigan and compounds set forth in U.S. Pat. No. 5,352,708), and neuroprotectants (e.g., compounds from U.S. Pat. No. 4,690,931, particularly eliprodil and R-eliprodil, as set forth in a pending application U.S. Ser. No. 60/203,350, and appropriate compounds from WO94/13275, including memantine.

The preferred compounds of Formula I are described in Examples 1 and 2. The most preferred compound is in Example 1. Examples of formulations anticipated to be suitable for delivery of this compound to the eye are provided.

EXAMPLE 1

3-(2-Aminopropyl)-1H-indazol-5-ol hydrochloride

Step A: 1-[5-Benzyloxy-3-(2-oxopropyl)indazol-1-yl]-ethanone

A mixture of (5-benzyloxy-1H-indazol-3-yl)-acetic acid (2 g, 7.08 mmol) and sodium acetate (0.99 g, 12 mmol) in acetic anhydride (6 ml) was stirred at 130° C. for 3 h. After cooling, water (15 ml) and ethyl acetate (15 ml) were added to the reaction mixture. The aqueous layer was separated and extracted with ethyl acetate (2×15 ml). The combined extracts were washed with saturated aqueous NaHCO$_3$ (2×20 ml) and saturated aqueous NaCl (20 ml), dried (MgSO$_4$), and evaporated to a residue which was purified by chromatography (silica, 15% ethyl acetate in hexane) to give a yellow solid (0.48 g): $^1$H NMR (CD$_3$OD) δ 8.35–8.30 (m, 1H), 7.48–7.23 (m, 6H), 7.04–7.02 (m, 2H), 5.11 (s, 2H), 4.02 (s, 2H), 2.77 (s, 3H), 2.27 (s, 3H); $^{13}$C NMR (CDCl$_3$)δ 203.64 (C), 170.47 (C), 156.20 (C), 145.04 (C), 136.52 (C), 128.64 (CH), 128.31 (CH), 127.60 (CH), 120.51 (CH), 116.74 (CH), 102.26 (CH), 70.68 (CH$_2$), 42.76 (CH$_2$), 29.59 (CH$_3$), 22.77 (CH$_3$), MS(APCl) m/z 323 (M+H)$^+$.

Step B: 1-[5-Benzyloxy-3-(2-hydroxypropyl)-indazol-1-yl]-ethanone

To a solution of the product from Step A (0.13 g, 0.4 mmol) in methanol (8 ml) was added NaBH$_4$ (0.016 g, 0.4 mmol) and the mixture was stirred at room temperature for 20 min. A saturated aqueous solution of NH$_4$Cl (20 ml) and ethyl acetate (20 ml) were added to the reaction mixture. The aqueous layer was separated and extracted with ethyl acetate (3×15 ml). The combined extracts were washed with a saturated aqueous solution of NaCl (2×15 ml), dried (MgSO$_4$), and evaporated to give an oil (0.12 g). MS(APCl) m/z 325 (M+H)$^+$.

Step C: 1-[3-(2-Azido-propyl)-5-benzyloxy-indazol-1-yl]-ethanone

A solution of the product from Step B (0.12 g, 0.37 mmol) and methanesulfonyl chloride (0.04 ml, 0.48 mmol) in CH$_2$Cl$_2$ (5 ml) and under nitrogen was cooled to 0° C. and triethylamine (0.07 ml, 0.48 mmol) was added. The resulting mixture was stirred at 0° C. for 10 min followed by the addition of a saturated aqueous solution of NH$_4$Cl (20 ml) and ethyl acetate (20 ml). The aqueous layer was separated and extracted with ethyl acetate (2×5 ml). The combined extracts were washed with a saturated aqueous solution of NaCl (2×15 ml), dried (MgSO$_4$), and evaporated to a residue which was dissolved in DMF (3 ml). Sodium azide (0.08 g, 1.2 mmol) was added and the mixture was stirred at 70° C. for 18 h. After cooling, water (20 ml) and ether (20 ml) were added and the aqueous layer was separated and further extracted with ether (3×20 ml). The combined extracts were washed with a saturated aqueous solution of NaCl (3×15 ml), dried (MgSO$_4$), and evaporated to a residue that was purified by chromatography (silica, 10% ethyl acetate in hexane) to give a yellow oil (0.12 g). MS(ES) m/z 350 (M+H)$^+$.

Step D: 3-(2-Aminopropyl)-1H-indazol-5-ol hydrochloride

A solution of the product from Step C (0.12 g, 0.34 mmol) in methanol (20 ml) was shaken under a hydrogen atmosphere (35 psi) in the presence of 10% palladium-on-carbon (0.12 g) for 18 h. The catalyst was removed by filtration and the filtrate was evaporated to a residue, which was purified by chromatography to give an oil. Treatment of the oil with a 1 N solution of HCl in ethanol gave the hydrochloride salt as a colorless semi-solid (0.013 g): $^1$H NMR (CD$_3$OD) δ 7.34–7.30 (m, 1H), 7.05–6.98 (m, 2H), 7.04–7.02 (m, 2H), 3.68–3.58 (m, 1H), 3.19–3.05 (m, 2H), 1.19–1.16 (d, J=6 Hz, 3H), MS(ES) m/z 192 (M+H)$^+$. Treatment of the oil prepared by this procedure with fumaric acid gave the fumarate salt as a gray solid; mp 227–230° C. Analysis: Calculated for C$_{10}$H$_{13}$N$_3$O. C$_4$H$_4$O$_4$. 0.3H$_2$O: C, 53.77; H, 5.63; N, 13.43. Found: C, 53.83; H, 5.85; N, 13.34.

EXAMPLE 2

3-(2-Aminopr pyl)-1-methyl-1H-indazol-5-ol fumarate

Step A. 1-(5-Benzyloxy-1H-indazol-3-yl)-propan-2-one

A solution of the product from Step 1 of Example 1 (2.0 g, 6.2 mmol) and sodium hydroxide (0.3 g, 7.5 mmol) in a mixture of methanol (15 ml) and water (15 ml) was stirred for 18 h at room temperature. The reaction mixture was extracted with ethyl acetate (4×30 ml) and the combined extracts were washed with brine, dried (MgSO$_4$), and evaporated to a residue which was purified by chromatography (silica, ethyl acetate/hexane, 1:1) to give a syrup (1.5 g): ESI/MS m/z 281 (M+H)$^+$.

Step B. 1-(5-Benzyloxy-1-methyl-1H-indazol-3-yl)-propan-2-one

To a solution of the product from Step A (1.2 g, 4.28 mmol) in DMF (10 ml) was added iodomethane (0.53 ml, 8.6 mmol) and potassium carbonate (1.2 g, 8.6 mmol); this mixture was stirred for 16 h at 70° C. After adding water (15 ml) and ethyl acetate (15 ml) to the reaction mixture, the aqueous layer was separated and extracted with ethyl acetate (3×20 ml). The combined extracts were washed with brine, dried (MgSO$_4$), and evaporated to a residue which was puified by chromatography (silica, ethyl acetate/hexane, 1:1) to give a viscous oil (0.6 g): APCl/LCMS m/z 295 (M+H)$^+$.

Step C.
3-(2-Aminopropyl)-1-methyl-1H-indazol-5-ol fumarate

The product of Step B (0.3 g, 0.1 mmol) was treated in the manner similar to that described in Example 1 Steps B through D to give an oil which was converted to the fumarate salt (0.071 g): mp 136–139° C.; LCMS m/z 206 (M+H)$^+$. Analysis. Calculated for C$_{11}$H$_{15}$N$_3$O.C$_4$H$_4$O$_4$. 0.1H$_2$O: C, 55.76; H, 5.98; N, 13.00. Found: C, 55.53; H, 6.11; N, 13.22.

EXAMPLE 3

2-Methyl-propionic acid 3-(2-aminopropyl)-1H-indazol-5-yl ester

Step A: 3-(2-(9-Fluorenylmethoxycarbonyl-amino)propyl)-1H-indazol-5ol

To a mixture of dioxane and water (4:1, 10 mL) was added 3-(2-aminopropyl)-1H-indazol-5-ol (0.10 g, 0.36 mmol), 9-fluorenylmethoxycarbonyl chloride (0.13 g, 0.54 mmol) and sodium bicarbonate (0.9 g, 0.54 mmol). The reaction mixture poured into dilute sodium bicarbonate and the resulting mixture extracted with ether. The combined organic extracts were dried (MgSO$_4$) and concentrated to a residue that was purified by chromatography.

Step B: 2-Methyl-propionic acid 3-(2-(9 fluorenyl-methoxycarbonylamino)propyl)-1H-indazol-5-yl ester To a solution of 3-(2-(9-fluorenylmethoxycarbonylamino) propyl)-1H-indazol-5-ol (0.17 g, 0.41 mmol) and diisopropylehtylamine (0.06 g, 0.50 mmol), in methylene chloride (10 mL) cooled at 0° C. is added 2-methylpropionyl chloride (0.05 g, 0.5 mmol) followed by 4-dimethylaminopyridine (0.05 g, 0.40 mmol). The reaction allowed to warm to room temperature and then is stirred at room temperature. The reaction mixture is added to dilute aqueous sodium bicarbonate and extracted with ether. The combined ether extracts are washed, dried (MgSO$_4$) and concentrated. The residue is purified by chromatography.

Step C: 2-Methyl-propionic acid 3-(2-aminopropyl)-1H-indazol-5-yl ester

A solution of 2-methyl-propionic acid 3-(2-(9fluorenyl-methoxycarbonylamino)propyl)-1H-indazol-5-yl ester (0.16 g, 0.33 mmol) in a 1:4 mixture of piperidine and dimethylformamide (2.5 mL) is stirred at ambient temperature. The reaction mixture is poured into dilute aqueous sodium bicarbonate and the resulting mixture is extracted first with ethyl acetate and then with methylene chloride. The combined organic extracts are dried (MgSO$_4$) and concentrated. The residue is purified by chromatography.

Receptor and binding agonist activity according to this invention can be determined using the following methods.

Method 1

5HT$_2$ Receptor Binding Assay

To determine the affinities of serotonergic compounds at the 5HT$_2$ receptors, their ability to compete for the binding of the agonist radioligand [$^{125}$I]DOI to brain 5HT$_2$ receptors is determined as described below with minor modification of the literature procedure [Neuropharmacology, 26, 1803 (1987)]. Aliquots of post mortem rat or human cerebral cortex homogenates (400 µl) dispersed in 50 mM Tris HCl buffer (pH 7.4) are incubated with [$^{125}$I]DOI (80 pM final) in the absence or presence of methiothepin (10 µM final) to define total and non-specific binding, respectively, in a total volume of 0.5 ml. The assay mixture is incubated for 1 hour at 23° C. in polypropylene tubes and the assays terminated by rapid vacuum filtration over Whatman GF/B glass fiber filters previously soaked in 0.3% polyethyleneimine using ice-cold buffer. Test compounds (at different concentrations) are substituted for methiothepin. Filter-bound radioactivity is determined by scintillation spectrometry on a beta counter. The data are analyzed using a non-linear, iterative curve-fitting computer program [Trends Pharmacol. Sci., 16, 413 (1995)] to determine the compound affinity parameter. The concentration of the compound needed to inhibit the [$^{125}$I]DOI binding by 50% of the maximum is termed the IC$_{50}$ or K$_i$ value.

Method 2

5HT$_2$ Functional Assay: Phosphoinositide (PI) turnover assay

The relative agonist activity of serotonergic compounds at the 5HT$_2$ receptor can be determined in vitro using the ability of the compounds to stimulate the production of [$^3$H]inositol phosphates in [$^3$H]myo-inositol-labeled A7r5 rat vascular smooth muscle cells by their ability to activate the enzyme phospholipase C. These cells are grown in culture plates, maintained in a humidified atmosphere of 5% CO$_2$ and 95% air and fed semi-weekly with Dulbecco's modified Eagle medium (DMEM) containing 4.5 g/l glucose and supplemented with 2 mM glutamine, 10 µg/ml gentamicin, and 10% fetal bovine serum. For the purpose of conducting the phosphoinositide (PI) turnover experiments, the A7r5 cells are cultured in 24-well plates as previously [J. Pharmacol. Expt. Ther., 286, 411 (1998)]. Confluent cells are exposed for 24–30 hrs to 1.5 µCi [$^3$H]-myo-inositol (18.3 Ci/mmol) in 0.5 ml of serum-free medium. Cells are then rinsed once with DMEM/F-12 containing 10 mM LiCl prior to incubation with the test agent (or solvent as the control) in 1.0 ml of the same medium for 1 hr at 37° C., after which the medium is aspirated and 1 ml of cold 0.1 M formic acid added to stop the reaction. The chromatographic separation of [$^3$H]-inositol phosphates ([$^3$H]-IPs) on an AG-1-X8 column is performed as previously described [J. Pharmacol. Expt. Ther. 286, 411 (1998)] with sequential washes with H$_2$O and 50 mM ammonium formate, followed by elution of the total [$^3$H]-IPs fraction with 1.2 M ammonium formate containing 0.1 M formic acid. The eluate (4 ml) is collected, mixed with 15 ml scintillation fluid, and the total [3H]-IPs determined by scintillation counting on a beta-counter. Concentration-response data are analyzed by the sigmoidal fit function of the Origin Scientific Graphics software (Microcal Software, Northampton, Mass.) to determine agonist potency (EC$_{50}$ value) and efficacy (Emax). Serotonin (5HT) is used as a positive control (standard) agonist compound and the efficacy of test compounds is compared to that of 5HT (set at 100%). The concentration of the compound needed to stimulate the production of [$^3$1H]-IPs by 50% of the maximum response is termed the EC$_{50}$ value.

The above procedures were used to generate the data shown in Table 1.

TABLE 1

5HT$_2$ Receptor Binding and Functional Data

| Compound | IC$_{50}$, nM | EC$_{50}$, nM | Efficacy (E$_{max}$, %) |
|---|---|---|---|
| 3-(2-Aminopropyl)-1H-indazol-5-ol hydrochloride | 2.5 | 1,210 | 97 |
| 3-(2-Aminopropyl)-1-methyl-1H-indazol-5-ol fumarate | — | 778 | 98 |

EXAMPLE 4

| Ingredients | Amount (wt %) |
|---|---|
| 3-(2-Aminopropyl)-1-methyl-1H-indazol-5-ol fumarate | 0.01–2% |
| Hydroxypropyl methylcellulose | 0.5% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH |
| Purified water | q.s. to 100% |

EXAMPLE 5

| Ingredients | Amount (wt %) |
|---|---|
| 3-(2-Aminopropyl)-1H-indazol-5-ol | 0.01–2% |
| Methyl cellulose | 4.0% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH |
| Purified water | q.s. to 100% |

EXAMPLE 6

| Ingredients | Amount (wt %) |
|---|---|
| 3-(2-Aminopropyl)-1H-indazol-5-ol | 0.01–2% |
| Guar gum | 0.4–6.0% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH |
| Purified water | q.s. to 100% |

EXAMPLE 7

| Ingredients | Amount (wt %) |
|---|---|
| 2-Methyl-propionic acid 3-(2-aminopropyl)-1H-indazol-5-ol ester | 0.01–2% |
| White petrolatum and mineral oil and lanolin | Ointment consistency |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH |

We claim:

1. A method for lowering and controlling normal or elevated intraocular pressure, which comprises administering a pharmaceutically effective amount of a compound of the formula:

FORMULA I wherein G is chosen from hydrogen, halogen, or $C_{1-4}$alkyl;
R is hydrogen, $C_{1-4}$alkyl, C(=O)W, or P(=O)(OX)(OY),
$R^1$ and $R^2$ are hydrogen;
$R^3$ and $R^4$ are independently chosen from hydrogen, $C_{1-4}$alkyl or $R^3$, $R^4$ and the carbon atom to which they are attached can form a cyclopropyl ring, or furthermore, $R^2$ and $R^3$ together can be $(CH_2)_m$ to form a saturated heterocycle;
when $R^2$ and $R^3$ are part of a heterocycle, $R^1$ can be hydrogen or $C_{1-4}$alkyl;
$R^5$ can be hydrogen or $C_{1-4}$alkyl;
when R, $R^1$, $R^2$, $R^5$, and G all are hydrogen $R^3$ and $R^4$ cannot both be hydrogen;
W is $C_{1-6}$alkyl, $NR^6R^7$, $N(R^6)CH_2(CH_2)_nC(=O)N(R^7)(R^8)$, $OC_{1-6}$alkyl, $C_{1-6}$alkyl (which can be substituted with halogen, hydroxyl, $CO_2C_{1-4}$alkyl, $CON(C_{1-4}$alkyl$)_2$,C(=NH)NH$_2$, HC(=NH)NH$_2$, NH$_2$), $C_{2-4}$alkenyl (substituted by phenyl, unsubstituted or substituted with one or more of $C_{1-4}$alkyl, $C_{1-4}$alkoxy or halogen);
$R^6$, $R^7$, $R^8$ are independently chosen from hydrogen or $C_{1-4}$alkyl;
X and Y are independently chosen from hydrogen, $C_{1-10}$ or alkyl or X and Y can together form a lower alkyl chain of $(CH_2)_m$;
m is 2–4;
n is 1 or 2;
and pharmaceutically acceptable salts and solvates of the compounds.

2. The method of claim 1 wherein the compound is defined as follows:
G is chosen from hydrogen, halogen, or $C_{1-4}$alkyl;
R is C(=O)W, or P(=O)(OX)(OY),
$R^1$ and $R^2$ are hydrogen;
$R^3$, $R^4$ and the carbon atom to which they are attached can form a cyclopropyl ring, or furthermore, $R^2$ and $R^3$ together can be $(CH_2)_m$ to form a saturated heterocycle;
when $R^2$ and $R^3$ are part of a heterocycle, $R^1$ can be hydrogen or $C_{1-4}$alkyl;
$R^5$ can be hydrogen or $C_{1-4}$alkyl;
W is $C_{1-6}$alkyl, $NR^6R^7$, $N(R^6)CH_2(CH_2)_nC(=O)N(R^7)(R^8)$, $C_{1-6}$alkyl (which can be substituted with halogen, hydroxyl, $CO_2C_{1-4}$alkyl, $CON(C_{1-4}$alkyl$)_2$, C(=NH)NH$_2$, HC(=NH)NH$_2$, NH$_2$), $C_{2-4}$alkenyl (substituted by phenyl, unsubstituted or substituted with one or more of $C_{1-4}$alkyl $C_{1-4}$alkoxy or halogen);
$R^6$, $R^7$, $R^8$ are independently chosen from hydrogen or $C_{1-4}$alkyl;
X and Y are independently chosen from hydrogen, $C_{1-10}$ alkyl or X and Y can together form a lower alkyl chain of $(CH_2)_m$;
m is 2–4:
n is 1 or 2.

3. The method of claim 1 wherein the compound is defined as follows:
G is chosen from hydrogen, halogen, or $C_{1-4}$alkyl;
R is hydrogen, C(=O)W, or P(=O)(OX)(OY),
$R^1$ and $R^2$ are hydrogen;
$R^3$ and $R^4$ are independently chosen from hydrogen, $C_{1-4}$alkyl or $R^3$, $R^4$ and the carbon atom to which they are attached can form a cyclopropyl ring;
$R^5$ can be hydrogen or $C_{1-4}$alkyl;
W is $C_{1-6}$alkyl, $NR^6R^7$, $N(R^6)CH_2(CH_2)_nC(=O)N(R^7)(R^8)$, $C_{1-6}$alkyl, (which can be substituted with halogen, hydroxyl, $CO_2C_{1-4}$alkyl, $CON(C_{1-4}$alkyl$)_2$, C(=NH)NH$_2$, HC(=NH)NH$_2$, NH$_2$), $C_{2-4}$alkenyl (substituted by phenyl, unsubstituted or substituted with one or more of $C_{1-4}$alkyl, $C_{1-4}$alkoxy or halogen);

R⁶, R⁷, R⁸ are independently chosen from hydrogen or C$_{1-4}$alkyl;

X and Y are independently chosen from hydrogen, C$_{1-10}$ alkyl or X and Y can together form a lower alkyl chain of (CH$_2$)$_m$;

m is 2 or 3;

n is 1 or 2.

4. The method of claim 1 wherein the compound is defined as follows:

G is chosen from hydrogen, halogen, or C$_{1-4}$alkyl;

R is hydrogen or C(=O)W;

R¹ and R² are hydrogen;

R³ is hydrogen and R⁴ is methyl or R³, R⁴ and the carbon atom to which they are attached form a cyclopropyl ring;

R⁵ is hydrogen;

W is C$_{1-6}$alkyl, C$_1$-alkyl (which can be substituted with halogen, hydroxyl, CON(C$_{1-4}$alkyl)$_2$, C(=NH)NH$_2$).

5. The method of claim 1 wherein the compound is selected from the group consisting of:

3-(2-aminopropyl)-1H-indazol-5-ol;

3-(2-aminopropyl)-1-methyl-1H-indazol-5-ol;

2-(5-methoxy-1H-indazol-3-yl)-1-methyl-ethylamine;

3-(2-aminopropyl)-6-fluoro-1H-indazol-5-ol;

3-(2-aminopropyl)-7-methyl-1H-indazol-5-ol;

3-(2-aminopropyl)-6-fluoro-1-methyl-1H-indazol-5-ol;

2-methyl-propionic acid 3-(2-aminopropyl)-1H-indazol-5-yl ester;

2,2-dimethyl-propionic acid 3-(2-aminopropyl)-1H-indazol-5-yl ester;

cyclopropanecarboxylic acid 3-(2-aminopropyl)-1H-indazol-5-yl ester;

N,N-diethyl-succinamic acid 3-(2-aminopropyl)-1H-indazol-5-yl ester.

\* \* \* \* \*